(12) United States Patent
Avram

(10) Patent No.: US 11,696,909 B2
(45) Date of Patent: Jul. 11, 2023

(54) PAIN-RELIEVING TOPICAL COMPOSITIONS

(71) Applicant: INNOCAN PHARMA LTD., Herzliya (IL)

(72) Inventor: Nir Avram, Metar (IL)

(73) Assignee: INNOCAN PHARMA LTD., Herzliya Pituach (IL)

( * ) Notice: Subject to any disclaimer, the term of this patent is extended or adjusted under 35 U.S.C. 154(b) by 219 days.

(21) Appl. No.: 16/968,627

(22) PCT Filed: Jul. 11, 2019

(86) PCT No.: PCT/IL2019/050776
§ 371 (c)(1),
(2) Date: Aug. 10, 2020

(87) PCT Pub. No.: WO2020/012480
PCT Pub. Date: Jan. 16, 2020

(65) Prior Publication Data
US 2021/0046040 A1    Feb. 18, 2021

Related U.S. Application Data

(60) Provisional application No. 62/696,341, filed on Jul. 11, 2018.

(51) Int. Cl.
| | |
|---|---|
| *A61K 31/352* | (2006.01) |
| *A61P 29/02* | (2006.01) |
| *A61K 9/00* | (2006.01) |
| *A61K 9/06* | (2006.01) |
| *A61K 31/045* | (2006.01) |
| *A61K 31/05* | (2006.01) |
| *A61K 31/125* | (2006.01) |
| *A61K 31/235* | (2006.01) |
| *A61K 47/02* | (2006.01) |

(52) U.S. Cl.
CPC .......... *A61K 31/352* (2013.01); *A61K 9/0014* (2013.01); *A61K 9/06* (2013.01); *A61K 31/045* (2013.01); *A61K 31/05* (2013.01); *A61K 31/125* (2013.01); *A61K 31/235* (2013.01); *A61K 47/02* (2013.01); *A61P 29/02* (2018.01)

(58) Field of Classification Search
CPC .................................................... A61K 31/352
See application file for complete search history.

(56) References Cited

U.S. PATENT DOCUMENTS

| 6,949,582 B1 | 9/2005 | Wallace |
| 9,717,757 B1 | 8/2017 | Gasque, Jr. |
| 2014/0018750 A1 | 1/2014 | Pagliaro et al. |
| 2015/0126595 A1 | 5/2015 | Smith |

FOREIGN PATENT DOCUMENTS

WO    2010126501 A1    11/2010

OTHER PUBLICATIONS

CBD Medic—Arthritis Deep Relief product information (total 3 pages).
Dragon Balm description (total 2 pages).
Ultra Strength Bengay Cream product information (total 7 pages).
Marinotti, Osvaldo, and Miles Sarill. "Differentiating full-spectrum hemp extracts from CBD isolates: Implications for policy, safety and science." Journal of Dietary Supplements 17.5 (2020): 517-526.
CBD vs Hemp Extract vs Hemp Seed Oil: Know What You Buy | Your Guide to Understanding CBD Oil, dated Apr. 6, 2022 (total of 4 pages) https://www.palmorganix.com/cbdvs-hemp-extract-vs-hemp-seed-oil-know-what-you-buy/.

*Primary Examiner* — Nizal S Chandrakumar
(74) *Attorney, Agent, or Firm* — JMB Davis Ben-David

(57) ABSTRACT

Described herein are compositions for topical use comprising active agents to provide pain relief. The compositions comprise a magnesium salt, a cannabinoid and at least one additional topical analgesic agent. Additionally described herein are methods for treating pain comprising administering to a person in need thereof a composition comprising a pharmaceutically effective amount of a cannabinoid, a magnesium salt and at least one of: methyl salicylate, and menthol.

13 Claims, No Drawings

PAIN-RELIEVING TOPICAL COMPOSITIONS

CROSS REFERENCE TO RELATED APPLICATIONS

This is the US National Stage of International Patent Application No. PCT/IL 2019/050776, filed on Jul. 11, 2019, which in turn claims benefit to U.S. Provisional Patent Application No. 62/696,341 filed Jul. 11, 2018; which is the incorporated by reference herein in its entirety.

FIELD

Provided herein are topical compositions for the alleviation of pain.

BACKGROUND

Pain is an unpleasant sensory and emotional experience associated with tissue damage. Pain is typically a symptom of an underlying disease or condition.

Pain may be treated through various methods. One of the methods of pain treatment is administration of an analgesic, a drug administered to alleviate pain in a subject. There are a number of groups of analgesic having various mechanisms of action. Some of these groups include opioids, COX-2 inhibitors, and other COX inhibitors, also known as non-steroidal anti-inflammatory drugs (NSAID).

An analgesic may be administered systemically, for example orally, in the form of a tablet or a syrup, or parenterally, in the form of an injection. Alternatively, analgesics may be administered topically, in the form of a cream, ointment, paste, gel, suspension, pump spray, aerosol spray, aerosol foam, liquid, powder, stick, or lotion. Some analgesics such as COX-2 inhibitors have been associated with side effects such as cardiovascular events and gastrointestinal bleeding. Topical administration of analgesics may be advantageous in limiting systemic exposure to analgesics, thereby reducing potential for side effects.

SUMMARY

Described herein are compositions for topical use comprising active agents to provide pain relief. The compositions comprise a magnesium salt, a cannabinoid and at least one additional topical analgesic agent.

Additionally described herein are methods for treating pain comprising administering to a person in need thereof a composition comprising a pharmaceutically effective amount of a cannabinoid, a magnesium salt and at least one of: methyl salicylate, and menthol.

Additionally described herein are methods for treating pain comprising administering to a person in need thereof such compositions are described herein.

The foregoing and other objects, features, and advantages will become more apparent from the following detailed description.

DETAILED DESCRIPTION

Unless otherwise noted, technical terms are used according to conventional usage. Definitions of common terms in pharmaceutical sciences can be found in Troy et al. *Remington: The Science and Practice of Pharmacy*. Published by Lippincott Williams & Wilkins, 2006. In case of conflict, the present specification, including explanations of terms, will control. In addition, all the materials, methods, and examples are illustrative and not intended to be limiting.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia and is used herein to indicate a non-limiting example. Thus, the abbreviation "e.g." is synonymous with the term "for example."

As mentioned above, embodiments relate to compositions comprise methyl salicylate, menthol, a magnesium salt and a cannabinoid. Without being bound by theory, it is suggested that cannabinoids will act synergistically with a magnesium salt and with the pain-relieving ingredients (methyl salicylate and/or others) to provide a pain relieving, soothing effect.

Methyl salicylate is the methyl ester of salicylic acid. It is produced by some plants and is known as wintergreen oil. Methyl salicylate is a commercially available compound and has been used topically to treat muscular pain and joint pain.

According to an embodiment, methyl salicylate may be present in an amount between about 0.1% and about 30% of the composition. Optionally, methyl salicylate may be present in an amount between about 10% and about 20% of the composition. Optionally, methyl salicylate may be present in an amount about 10% of the composition Optionally, methyl salicylate may be present in an amount about 15% of the composition.

Menthol is an organic, naturally occurring substance found in wild mint. It can be administered topically to provide a cooling, analgesic sensation when applied.

According to an embodiment, menthol may be present in an amount between about 0.1% and about 15% of the composition. Optionally, menthol may be present in an amount between about 2% and about 15% of the composition. Optionally, menthol may be present in an amount of about 10% of the composition. Optionally, menthol may be present in an amount of about 2% of the composition.

Magnesium salts are salts comprising magnesium as a cation. Magnesium salts, particularly magnesium chloride, have been used in topical applications to humans. Optionally, the magnesium salt is magnesium chloride, magnesium sulfate, magnesium bromide, magnesium carbonate, magnesium bicarbonate, magnesium hydroxide, magnesium L-pyrrolidone carboxylic acid (Mg-PCA), and magnesium oxide. Preferably the magnesium salt is magnesium sulfate or magnesium chloride. Most preferably the magnesium salt is magnesium chloride ($MgCl_2$). A hydrate of a magnesium salt may be used, for example, magnesium chloride hexahydrate. The amount of magnesium ion in the composition may be between about 0.25% to about 10% by weight of the composition, preferably between about 1% and about 6% of the composition. The amount of magnesium ion may be between about 4% and 6% of the composition.

A cannabinoid is a chemical compound that acts on cannabinoid receptors in cells in mammals, including in humans. Cannabinoids can be manufactured synthetically or obtained from various parts of the genus *Cannabis*, in particular, from the species *Cannabis Sativa*. Two preferred cannabinoids according to various embodiments, are (−)-trans-$\Delta^9$-tetrahydrocannabinol, and/or isomers thereof (THC) and cannabidiol (CBD). Alternatively, a cannabinoid may be in the form of hemp oil. Alternatively, a cannabinoid may be in the form of cannabis oil. Compositions described herein may comprise one cannabinoid or multiple cannabinoids, such as a combination of CBD and THC.

According to an embodiment, a cannabinoid may be present in an amount between about 0.1% and about 10% of the composition. Optionally, a cannabinoid may be present in an amount between about 0.1% and 1% of the composition. Optionally, the cannabinoid may be present in an amount between 0.45% and 0.55% of the composition, preferably 0.5% of the composition.

Optionally, the composition may further comprise camphor. The camphor may be present in an amount between about 0.1% and about 10% of the composition, optionally between about 2% and about 5% of the composition, optionally about 4% of the composition.

According to an embodiment, the composition may comprise a magnesium salt, a cannabinoid and at least one additional topical analgesic agent. The at least one additional topical analgesic agent may be selected from the group consisting of: alcohol, ethoxylated alkyl alcohol, allantoin, allyl isothiocyanate, aluminum acetate, aluminum chloride hexahydrate, aluminum hydroxide, ammonia solution, aspirin, benzalkonium chloride, benzethonium chloride, benzocaine, benzyl alcohol, bismuth sodium tartrate, bithionol, butamben picrate, calamine, camphor, camphorated metacresol, capsaicin, capsicum, capsicum oleoresin, cetalkonium chloride, chloral hydrate, chlorobutanol, chlorpheniramine maleate, creosote, cupric sulfate, cyclomethycaine sulfate, dexpanthenol, dibucaine, dimethisoquin hydrochloride, diperodon hydrochloride, diphenhydramine hydrochloride, dyclonine hydrochloride, ephedrine hydrochloride, ergot fluid extract, eucalyptus oil, eugenol, ferric chloride, glycerin, glycol salicylate, hectorite, hexylresorcinol, histamine dihydrochloride, hydrocortisone, hydrocortisone acetate, hydrogen peroxide, *Impatiens biflora* tincture, iron oxide, isopropyl alcohol, juniper tar, lanolin, lidocaine, menthol, merbromin, methapyrilene hydrochloride, methyl nicotinate, methyl salicylate, panthenol, parethoxycaine hydrochloride, pectin, peppermint oil, phenol, phenolate sodium, phenyltoloxamine dihydrogen citrate, povidone-vinylacetate copolymers, pramoxine hydrochloride, pyrilamine maleate, resorcinol, salicylamide, simethicone, sodium bicarbonate, sodium borate, sulfur, tannic acid, tetracaine, thymol, topical starch, tripelennamine hydrochloride, trolamine, trolamine salicylate (trietnanolamine salicylate), turpentine oil, zinc acetate, zinc oxide, zinc sulfate, zirconium oxide and zyloxin.

According to an embodiment, the composition may be in the form of a cream, ointment, paste, gel, suspension, pump spray, aerosol spray, non-pressurized spray, continuous spray, non-chlorofluorocarbon-based spray, aerosol foam, liquid, solution, powder, stick, roll-on or lotion.

In addition to active ingredients, compositions described herein may further comprise at least one inert ingredient. The inert ingredient may be selected from the group consisting of: water, a solvent, an emulsifier, an emollient, a moisturizer, a pH adjustment agent, a polymer, a humectant, an occlusive agent, a preservative, a thickener, an anti-irritation agent, a conditioning agent, a buffer, a vitamin, an extract, a natural oil, a wax, a penetration enhancer, a peptide, a sugar derivative, a fatty acid, a fatty alcohol, a silicone, a polyethyl-glycol, a fragrance, a pigment, an ester, a triglyceride, a butter, hyaluronic acid, and an absorbing powder.

The preservative may be selected from the group consisting of: a parahydroxybenzoic acid, methylparaben, propylparaben, Benzyl Alcohol, Phenoxyethanol, Ethylhexylglycerin, Octanediol, Hexanediol, Pentandiol, Sorbitan Caprylate, capralyl glycol, caprylhydroxamic acid, Phenoxyethanol Triethylene glycol, sodium benzoate, and Bronopol.

As described herein, certain embodiments relate to methods for treatment of pain comprising administering to a patient in need thereof a composition comprising a pharmaceutically effective amount of methyl salicylate, menthol, a magnesium salt and a cannabinoid. According to an embodiment, the methods relieve pain, provide muscle relief, provide topical anesthesia, provide topical analgesia or have an antipruritic effect. Optionally the compositions may be used for temporary relief of pain and/or itching associated with minor burns, sunburn, minor cuts, scrapes, insect bites or minor skin irritations and for temporary protection from minor skin irritation. Optionally, the compositions may be used for alleviating joint pain. Optionally, the compositions may be used for alleviating pain associated with backache, arthritis, strains, bruises, back pain, neck pain, knee pain, foot pain, or sprains.

According to an embodiment, the composition may be applied between once and 4 times daily.

According to an embodiment, the composition may be applied in a dosage of between about 0.1 milliliter (ml) and about 10.0 ml per application.

According to an embodiment, the composition is a cream for topical administration. According to an embodiment, the composition is a biphasic composition, adapted for packaging in a spray bottle. Optionally, the spray bottle is configured to be shaken before use, to combine both phases of the composition.

The following examples are provided to illustrate certain particular features and/or embodiments. These examples should not be construed to limit the disclosure to the particular features or embodiments described.

EXAMPLES

Example 1A: Attempts to Prepare Oil in Water Cream Compositions

A composition is prepared using the ingredients listed in Table 1:

TABLE 1

| Ingredient | Function | Amount (weight percent) |
|---|---|---|
| Water | Aqueous solvent | 49.6 |
| Glycerin 99.7% | Humectant | 4.0 |
| Magnesium PCA | Pain relief/ muscle relaxation | 0.4 |
| Glyceryl stearate | Emulsifier | 3.5 |
| Stearic Acid | Emulsifier/thickener | 1.5 |
| Cetyl Alcohol | Thickener | 3.0 |
| Stearyl Alcohol | Thickener | 3.0 |
| Isopropyl alcohol | Solvent | 3.0 |
| Potassium cetyl phosphate | Emulsifier | 1.0 |
| Euxyl PE 9010 (Phenoxyethanol and ethylhexylglycerin) | Preservative | 1.0 |

TABLE 1-continued

| Ingredient | Function | Amount (weight percent) |
|---|---|---|
| Hemp oil, 10% CBD | Pain relief | 5.0 |
| Methyl salicylate | Pain relief | 15.0 |
| Menthol | Cooling and pain relief | 10.0 |
| Total | | 100 |

Water is added to glycerin and heated to 65° C. Magnesium is added, and the mixture is mixed. In a separate vessel the oil phase is prepared using glyceryl stearate, stearic acid, cetyl alcohol, stearyl alcohol, isopropyl alcohol, potassium cetyl phosphate, Euxyl PE 9010 and hemp oil, which are heated to 65° C. and mixed until all solids and waxes are dissolved. The water phase and oil phase are combined and homogenized for 15 minutes. Homogenizing is stopped, and the mixture is cooled while mixing. At a temperature of 55° C., the active ingredients methyl salicylate and menthol are added and homogenized for 2 minutes. Cooling is then continued while gently mixing to a temperature of 35° C. The pH is measured then adjusted with triethanolamine or lactic acid to achieve a pH of 5.0-6.5.

The viscosity is measured to be between 10,000-40,000 centipoise (cps). The amount of CBD in the composition is between 0.45-0.55%. The amount of menthol in the composition is between 9.0-11.0%. The amount of methyl salicylate in the composition is between 13.5 and 16.5%.

The compositions prepared lacked stability, and the emulsion was broken, causing phase separation within two months of preparation.

Example 1B: Additional Attempts to Prepare Oil in Water Emulsions in Cream Form

A composition is prepared using the ingredients listed in Table 2:

TABLE 2

| Ingredient | Function | Amount (weight percent) |
|---|---|---|
| Water | Aqueous solvent | 52.6 |
| Glycerin 99.7% | Humectant | 3.0 |
| Magnesium Aluminum Silicate | Pain relief/ muscle relaxation | 1.00 |
| Polysorbate 80 | Emulsifier/solubilizer | 0.50 |
| Arlacel 165 (glycerol monostearate + PEG-100 Stearate) | Emulsifier (oil in water) | 3.50 |
| Stearic Acid | Emulsifier/thickener | 1.5 |
| Cetyl Alcohol | Thickener | 2.5 |
| Stearyl Alcohol | Thickener | 3.0 |
| Hemp oil, 10% CBD | Pain relief | 5.0 |
| Potassium cetyl phosphate | Emulsifier | 1.0 |
| Euxyl PE 9010 (Phenoxyethanol and ethylhexylglycerin) | Preservative | 1.0 |
| Methyl salicylate | Pain relief | 15.0 |
| Menthol | Cooling and pain relief | 10.0 |
| Magnesium PCA | Pain relief | 0.4 |
| Total | | 100 |

Water is added to glycerin and magnesium aluminum silicate and is heated to 75° C. and homogenized to form a homogenous gel. In a separate vessel the oil phase is prepared using Polysorbate 80, arlacel, stearic acid, cetyl alcohol, stearyl alcohol, hemp oil, potassium cetyl phosphate, and Euxyl PE 9010, which are heated to 65° C. and mixed until all solids and waxes are dissolved. The water phase and oil phase are combined and homogenized for 15 minutes. Homogenizing is stopped, and the mixture is cooled while mixing. At a temperature of 55° C., the active ingredients methyl salicylate and menthol are added and homogenized for 2 minutes. Cooling is then continued while gently mixing to a temperature of 35° C. The pH is measured then adjusted with triethanolamine or lactic acid to achieve a pH of 5.0-6.5.

The viscosity is measured to be between 15,000 and 30,000 cps. The amount of CBD in the composition is between 0.45-0.55%. The amount of menthol in the composition is between 9.0-11.0%. The amount of methyl salicylate in the composition is between 13.5 and 16.5%.

The compositions prepared lacked stability, and the emulsion was broken, causing phase separation within less than one week from preparation.

Attempts to prepare compositions having high concentrations of magnesium salts, which are water soluble, with additional active ingredients, such as cannabinoids, in oil in water emulsions, were not successful in preparing stable creams. Additional attempts to prepare oil in water emulsions were unsuccessful using various concentrations of magnesium salts and alternate emulsifiers.

Example 2A: Preparation of Water in Oil Emulsion

A composition is prepared using the ingredients listed in Table 3:

TABLE 3

| Ingredient | Function | Amount (weight percent) |
|---|---|---|
| Water | Aqueous solvent | 37.3 |
| Magnesium Chloride | Pain relief/ muscle relaxation | 10.0 |
| Propylene Glycol | Solvent | 10.0 |
| Alcohol (absolute) | Solvent | 10.0 |
| Menthol | Pain Relief | 10.0 |
| SF1540 (Cyclopentasiloxane and PEG/PPG-20/15 dimethicone) | Emulsifier | 3.0 |
| Hemp oil (10% CBD) | Pain Relief | 5.0 |
| Cyclopentasiloxane | Lubricant | 14.7 |

The SF1540 is combined with hemp oil and cyclopentasiloxane until a homogenous liquid is obtained. In a separate container, magnesium chloride is dissolved in water. In another separate vessel menthol is dissolved in alcohol and propylene glycol. The water phase and the propylene glycol phases are combined until a clear solution is obtained. While mixing the hemp oil containing phase, the clear aqueous/propylene glycol solution is added slowly. After combining, the phases are mixed vigorously for 5 minutes, then homogenized at high speed for 5 minutes until a stable emulsion is formed.

The pH is measured then adjusted with triethanolamine or lactic acid to achieve a pH of 5.0-6.5.

The viscosity is measured to be between 2,000 and 6,000 cps. The amount of CBD in the composition is between 0.45-0.55%. The amount of menthol in the composition is between 9.0-11.0%.

Example 2B: Additional Cream Compositions, Water in Oil Emulsion

A composition is prepared using the ingredients listed in Table 4:

TABLE 4

| Ingredient | Function | Amount (weight percent) |
|---|---|---|
| Water | Aqueous solvent | 37.0 |
| Magnesium Chloride | Pain relief/ muscle relaxation | 10.0 |
| Propylene Glycol | Solvent | 10.0 |
| Alcohol (absolute) | Solvent | 10.0 |
| Menthol | Pain Relief | 10.0 |
| SF1540 (Cyclopentasiloxane and PEG/PPG-20/15 dimethicone) | Emulsifier | 3.0 |
| Hemp oil (10% CBD) | Pain Relief | 5.0 |
| Methyl Salicylate | Pain Relief | 15.0 |

The SF1540 is combined with hemp oil and methyl salicylate until a homogenous liquid is obtained. In a separate container, magnesium chloride is dissolved in water. In another separate container menthol is dissolved in alcohol and propylene glycol. The water phase and the propylene glycol phases are combined until a clear solution is obtained. While mixing the hemp oil containing phase, the clear aqueous/propylene glycol solution is added slowly. After combining, the phases are mixed vigorously for 5 minutes, then homogenized at high speed for 5 minutes until a stable emulsion is formed.

The pH is measured then adjusted with triethanolamine or lactic acid to achieve a pH of 5.0-6.5.

The viscosity is measured to be between 2,000 and 6,000 cps. The amount of CBD in the composition is between 0.45-0.55%. The amount of menthol in the composition is between 9.0-11.0%. The amount of methyl salicylate in the composition is between 13.5 and 16.5%.

The water in oil compositions prepared in examples 2A and 2B were stable, despite relatively high magnesium concentrations. They maintained stability of the emulsion even at a relative humidity of 75% and temperature of 40° C. for three months.

Water in oil compositions such as those described in the above examples may be packaged in a roll-on container for easy application to the skin of a patient in need thereof.

In addition to emulsifiers described in examples 2A and 2B, other emulsifiers which may be used include: Dow Corning® 5225C, comprising 12.5% dispersion of high molecular weight silicone polyether in decamethylcyclopentasiloxane; ABIL® EM 90 (Cetyl PEG/PPG-10/1 Dimethicone); and Dow Corning® ES-5300, Lauryl PEG-10 Tris (trimethylsiloxy) silylethyl Dimethicone.

Example 3A

Compositions for Topical Administration

Spray on composition, configured to be introduced into a pump-spray bottle, shaken, and then sprayed on, is prepared using the ingredients listed in Table 5.

TABLE 5

| Ingredient | Function | Amount (weight percent) |
|---|---|---|
| Water | Aqueous solvent | 37.0 |
| Magnesium Chloride Hexahydrate | Pain relief/ muscle relaxation | 34.0 |
| Menthol | Pain Relief | 2.0 |
| Methyl Salicylate | Pain Relief | 10.0 |
| Denatured Ethanol SD#40 | Solvent | 10.0 |
| Polysorbate-20 (Tween-20) | Emulsifier | 2.0 |
| Hemp oil, 10% CBD | Pain Relief | 5.0 |

Water is added to magnesium chloride salt and mixed to form a clear solution. In a separate container, menthol, methyl salicylate and ethanol are mixed until dissolution. The alcoholic phase and aqueous phases are combined. Then, in a separate vessel, hemp oil is mixed with Polysorbate-20, and then added to the combined alcoholic and aqueous phase while mixing and homogenizing. A white lotion is formed.

Example 3B

Compositions for Topical Administration

Spray on composition, configured to be introduced into a pump-spray bottle, shaken, and then sprayed on, is prepared using the ingredients listed in Table 6.

TABLE 6

| Ingredient | Function | Amount (weight percent) |
|---|---|---|
| Water | Aqueous solvent | 34.0 |
| Magnesium Chloride Hexahydrate | Pain relief/ muscle relaxation | 34.0 |
| Menthol | Pain Relief | 5.0 |
| Propylene Glycol | Solubilizer/Humectant | 10.0 |
| Denatured Ethanol SD#40 | Solvent | 10.0 |
| Polysorbate-20 (Tween-20) | Emulsifier | 2.0 |
| Hemp oil, 10% CBD | Pain Relief | 5.0 |

Water is added to magnesium chloride salt and mixed to form clear solution. In a separate container, propylene glycol, methyl salicylate and ethanol are mixed until dissolution. The alcoholic phase and aqueous phases are combined. Then, in a separate vessel, hemp oil is mixed with Polysorbate-20, and then added to the combined alcoholic and aqueous phase while mixing. A white lotion is formed.

Example 3C

Compositions for Topical Administration

Spray on composition is prepared using the ingredients listed in Table 7.

TABLE 7

| Ingredient | Function | Amount (weight percent) |
|---|---|---|
| Water | Aqueous solvent | 35.0 |
| Magnesium Chloride Hexahydrate | Pain relief/ muscle relaxation | 34.0 |
| Menthol | Pain Relief | 2.0 |
| Methyl Salicylate | Pain Relief | 10.0 |
| Camphor | Pain Relief | 2.0 |
| Denatured Ethanol SD#40 | Solvent | 10.0 |

TABLE 7-continued

| Ingredient | Function | Amount (weight percent) |
|---|---|---|
| Polysorbate-20 (Tween-20) | Emulsifier | 2.0 |
| Hemp oil, 10% CBD | Pain Relief | 5.0 |

Water is added to magnesium chloride salt and mixed to form a clear solution. In a separate container, menthol, camphor, methyl salicylate and ethanol are mixed until dissolution. The alcoholic phase and aqueous phases are combined. Then, in a separate vessel, hemp oil is mixed with Polysorbate-20, and then added to the combined alcoholic and aqueous phase while mixing. A white lotion is formed.

Example 3D

Compositions for Topical Administration

Spray on composition is prepared using the ingredients listed in Table 8.

TABLE 8

| Ingredient | Function | Amount (weight percent) |
|---|---|---|
| Water | Aqueous solvent | 26.0 |
| Magnesium Chloride Hexahydrate | Pain relief/muscle relaxation | 45.0 |
| Menthol | Pain Relief | 2.0 |
| Methyl Salicylate | Pain Relief | 10.0 |
| Denatured Ethanol SD#40 | Solvent | 10.0 |
| Polysorbate-20 (Tween-20) | Emulsifier | 2.0 |
| Hemp oil, 10% CBD | Pain Relief | 5.0 |

Water is added to magnesium chloride salt and mixed to form a clear solution. In a separate container, menthol, methyl salicylate and ethanol are mixed until dissolution. The alcoholic phase and aqueous phases are combined. Then, in a separate vessel, hemp oil is mixed with Polysorbate-20, and then added to the combined alcoholic and aqueous phase while mixing. A white lotion is formed.

Example 3E

Compositions for Topical Administration

Spray on composition is prepared using the ingredients listed in Table 9.

TABLE 9

| Ingredient | Function | Amount (weight percent) |
|---|---|---|
| Water | Aqueous solvent | 37.0 |
| Magnesium Chloride Hexahydrate | Pain relief/muscle relaxation | 34.0 |
| Menthol | Pain Relief | 2.0 |
| Methyl Salicylate | Pain Relief | 10.0 |
| Denatured Ethanol SD#40 | Solvent | 10.0 |
| Solubilisant LRI | Emulsifier/Solvent | 2.0 |
| Hemp oil, 10% CBD | Pain Relief | 5.0 |

Solubisant LRI is an excipient provided by Sensient Cosmetic Technologies, and containing PPG-26-Buteth-26 (and) PEG-40 Hydrogenated Castor Oil (and) Water. Water is added to magnesium chloride salt and mixed to form clear solution. In separate container, menthol, methyl salicylate and ethanol are mixed until dissolution. The alcoholic phase and aqueous phases are combined. Then, in a separate vessel, hemp oil is mixed with Solubilisant LRI, and then added to the combined alcoholic and aqueous phase while mixing. A white lotion is formed.

Example 3F

Compositions for Topical Administration

Spray on composition is prepared using the ingredients listed in Table 10.

TABLE 10

| Ingredient | Function | Amount (weight percent) |
|---|---|---|
| Water | Aqueous solvent | 36.70 |
| Allantoin | Anti allergic | 0.20 |
| Magnesium Chloride Hexahydrate | Pain Relief | 34.0 |
| Menthol | Pain Relief | 2.0 |
| Methyl Salicylate | Pain Relief | 10.0 |
| Bisabolol | Soothing agent | 0.10 |
| Denatured Ethanol SD#40 | Solvent | 10.0 |
| Solubilisant LRI | Solubilizer | 2.0 |
| Hemp oil, 10% CBD | Pain Relief | 5.0 |

Water is added to Allantoin, and mixed. Then magnesium chloride salt is added and mixed to form a clear solution. In a separate container, menthol, methyl salicylate, bisabolol, and ethanol are mixed until dissolution. The alcoholic phase and aqueous phases are combined. Then, in a separate vessel, hemp oil is mixed with Solubilisant LRI, and then added to the combined alcoholic and aqueous phase while mixing. A white lotion is formed.

In examples 3A-3F, a spray-on, pain relieving composition is prepared. The amount of CBD in the composition is between 0.45 and 0.55 g per 100 g of composition. The composition formed is a white lotion, having a viscosity of 100 cps or less. The composition can be applied to a patient in need of pain relief by spraying for example, from a spray bottle onto skin. The phases of the composition may separate over time. In order to make sure that the composition is sprayed in a uniform fashion, the spray bottle may contain instructions to direct the user to shake the bottle before spraying onto the skin.

The compositions described in examples 3A-3F have been found to be free of sediments and free of salt crystals. When sprayed on the skin, the drops are small and uniformly spread. The compositions are not sticky, and dry quickly when applied to the skin. They have been found to be useful by athletes and others who perform outdoor activities. The compositions are also advantageous in that they do not leave an oily residue on the skin, and are easily applied to areas of the skin.

An embodiment of the invention relates to a topical pharmaceutical composition comprising a magnesium salt, a cannabinoid and at least one additional topical analgesic agent. Optionally, the at least one additional topical analgesic agent is selected from the group consisting of: alcohol, ethoxylated alkyl alcohol, allantoin, allyl isothiocyanate, aluminum acetate, aluminum chloride hexahydrate, aluminum hydroxide, ammonia solution, aspirin, benzalkonium chloride, benzethonium chloride, benzocaine, benzyl alcohol, bismuth sodium tartrate, bithionol, butamben picrate, calamine, camphor, camphorated metacresol, capsaicin, capsicum, capsicum oleoresin, cetalkonium chloride, chloral hydrate, chlorobutanol, chlorpheniramine maleate, creosote, cupric sulfate, cyclomethycaine sulfate, dexpanthenol, dibucaine, dimethisoquin hydrochloride, diperodon hydrochloride, diphenhydramine hydrochloride, dyclonine hydrochloride, ephedrine hydrochloride, ergot fluid extract, eucalyptus oil, eugenol, ferric chloride, glycerin, glycol salicylate, hectorite, hexylresorcinol, histamine dihydrochloride, hydrocortisone, hydrocortisone acetate, hydrogen peroxide, *Impatiens biflora* tincture, iron oxide, isopropyl alcohol, juniper tar, lanolin, lidocaine, menthol, merbromin, methapyrilene hydrochloride, methyl nicotinate, methyl salicylate, panthenol, parethoxycaine hydrochloride, pectin, peppermint oil, phenol, phenolate sodium, phenyltoloxamine dihydrogen citrate, povidone-vinylacetate copolymers, pramoxine hydrochloride, pyrilamine maleate, resorcinol, salicylamide, simethicone, sodium bicarbonate, sodium borate, sulfur, tannic acid, tetracaine, thymol, topical starch, tripelennamine hydrochloride, trolamine, trolamine salicylate (trietnanolamine salicylate), turpentine oil, zinc acetate, zinc oxide, zinc sulfate, zirconium oxide and zyloxin. Optionally, the additional topical analgesic agent is selected from the group consisting of: methyl salicylate, menthol and camphor. Optionally, the composition comprises methyl salicylate and menthol. Optionally, the cannabinoid is Optionally, the cannabinoid is present in an amount between about 0.1% and about 10% of the composition. Optionally, the cannabinoid is present in an amount between about 0.1% and about 2% of the composition. Optionally, the cannabinoid is present in an amount of about 0.5% of the composition. Optionally, the methyl salicylate is present in an amount between about 0.1% and about 30% of the composition. Optionally, the methyl salicylate is present in an amount between about 10% and about 20% of the composition. Optionally, the methyl salicylate is present in an amount of about 15% of the composition. Optionally, the methyl salicylate is present in an amount of about 10% of the composition. Optionally, magnesium ion in the composition is present in an amount between about 0.025% and about 10% of the composition. Optionally, magnesium ion in the composition is present in an amount between 0.25% and 9% of the composition. Optionally, magnesium ion in the composition is present in an amount of about 1% to 6% of the composition. Optionally, magnesium ion in the composition is present in an amount of about 4% to 6% of the composition Optionally, the magnesium ion is added to the composition in the form of magnesium chloride, magnesium sulfate, magnesium bromide, magnesium carbonate, magnesium bicarbonate, magnesium hydroxide, magnesium oxide, magnesium L-pyrrolidone carboxylic acid, or hydrates thereof. Optionally, the magnesium ion is added to the composition in the form of magnesium chloride or a hydrate thereof. Optionally, the menthol is present in an amount between about 0.1% and about 15% of the composition. Optionally, the menthol is present in an amount between about 2% and about 15% of the composition. Optionally, the menthol is present in an amount of about 10% of the composition. Optionally, the menthol is present in an amount of about 2% of the composition. Optionally, the composition further comprises camphor. Optionally, camphor is present in an amount between about 0.1% and about 10% of the composition. Optionally, camphor is present in an amount between about 2% and about 5% of the composition. Optionally, the camphor is present in an amount of about 4% of the composition. Optionally, the composition is in the form of a spray, continuous spray, non-chlorofluorocarbon-based spray, aerosol foam, liquid, solution, powder, stick, roll-on, ointment, paste, or lotion. Optionally, the composition is in the form of a cream, wherein the viscosity is between 10,000 and 150,000 cps. Optionally, the composition is in the form of a spray, wherein the viscosity is between 10 and 1,000 cps. Optionally, the composition is in the form of a roll-on, wherein the viscosity is between 800 and 10,000 cps. Optionally, the composition further comprising an inert ingredient selected from the group consisting of: water, a solvent, an emulsifier, an emollient, a moisturizer, a pH adjustment agent, a polymer, a humectant, an occlusive agent, a preservative, a thickener, an anti-irritation agent, a conditioning agent, a buffer, a vitamin, an extract, a natural oil, a wax, a penetration enhancer, a peptide, a sugar derivative, a fatty acid, a fatty alcohol, a silicone, a polyethyl-glycol, a fragrance, a pigment, an ester, a triglyceride and an absorbing powder. Optionally, the composition is in the form of an emulsion. Optionally, the pH of the composition is between 5.5 and 7.0. Optionally, the cannabinoid is CBD and the composition has less than 10 mg/g of THC. Optionally, the composition is free of THC. Optionally, the emulsion remains stable for at least three months at 401 Wand 75% relative humidity. Optionally, the composition further comprises at least 10% propylene glycol. Optionally, the compositions further comprises cyclopentasiloxane. Optionally, the amount of cyclopentasiloxane is in an amount of between 5-15%. Optionally, the composition further comprising between 5-20% ethyl alcohol.

Some embodiments relate to a kit comprising a composition as described above, and instructions, wherein the composition is a biphasic composition comprising an oil phase and an aqueous phase and the composition is enclosed in a container, and wherein the instructions instruct to shake the container before administration of the composition.

Some embodiments relate to a method for treatment of pain comprising topically administering to a patient in need thereof, a composition described above. Optionally, the pain is pain and/or itching associated with minor burns, sunburn, minor cuts, scrapes, insect bites or minor skin irritations, muscle pain, joint pain, backache, arthritis, strains, bruises, back pain, neck pain, knee pain, foot pain, or sprains. Optionally, the composition is administered in an amount of between 0.1 ml and 10.0 ml per application. Optionally, the composition is administered between once and 4 times daily. Optionally, the patient shakes the composition before administration.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A topical pharmaceutical composition comprising a magnesium chloride, cannabidiol (CBD), an emulsifier, and at least one additional topical analgesic agent, selected from the group consisting of methyl salicylate, menthol, and camphor; wherein magnesium ion in the composition is present in an amount of 1% to 6% of the composition, and wherein the cannabinoid is present in an amount between 0.45% and 0.55% of the composition as hemp oil containing 10% CBD, and wherein the composition is a water-in-oil emulsion.

2. The composition according to claim 1, where in the composition comprises methyl salicylate and menthol.

3. The composition according to claim 1 wherein magnesium ion in the composition is present in an amount of 1% to 4% of the composition.

4. The composition according to claim 1 in the form of a cream, spray, continuous spray, non-chlorofluorocarbon-based spray, aerosol foam, liquid, solution, powder, stick, roll-on, ointment, paste, or lotion.

5. The composition according to claim 4 in the form of a cream, wherein the viscosity is between 10,000 and 150,000 cps.

6. The composition according to claim 4 in the form of a spray, wherein the viscosity is between 10 and 1,000 cps.

7. The composition according to claim 4 in the form of a roll-on, wherein the viscosity is between 800 and 10,000 cps.

8. The composition of claim 1 wherein the emulsion remains stable for at least three months at 40° C. and 75%.

9. The composition of claim 1 wherein the emulsifier is selected from the group consisting of: Cyclopentasiloxane, PEG/PPG-20/15 dimethicone, Cetyl PEG/PPG-10/1 Dimethicone, Lauryl PEG-10 Tris(trimethylsiloxy) silylethyl Dimethicone.

10. The composition of claim 1 wherein the emulsifier is Polysorbate-20.

11. The composition of claim 1 wherein the emulsifier is present in an amount of 3% of the composition.

12. The composition of claim 1 wherein the emulsifier is present in an amount of 2% of the composition.

13. The composition of claim 1 wherein CBD is present in an amount of 0.5% of the composition.

\* \* \* \* \*